(12) United States Patent
Likavec et al.

(10) Patent No.: US 6,169,185 B1
(45) Date of Patent: Jan. 2, 2001

(54) INK JET PRINTING INKS

(75) Inventors: Wayne R. Likavec, Parma; Apparao Jatla, Broadview Hts.; John F. Waters, Lakewood, all of OH (US)

(73) Assignee: Day-Glo Color Corp., Cleveland, OH (US)

( * ) Notice: Under 35 U.S.C. 154(b), the term of this patent shall be extended for 0 days.

(21) Appl. No.: 09/257,898

(22) Filed: Feb. 25, 1999

(51) Int. Cl.$^7$ ............................ C09B 57/02; C07D 405/04
(52) U.S. Cl. ............................................. 548/305.1
(58) Field of Search ........................................ 548/305.1

(56) References Cited

U.S. PATENT DOCUMENTS

| | | | |
|---|---|---|---|
| 2,600,375 | 6/1952 | Ackermann | 549/288 |
| 3,660,424 | 5/1972 | Kabas, et al. | 548/364.4 |
| 3,766,199 | * 10/1973 | Dehnert et al. | 548/305.1 X |
| 3,880,885 | 4/1975 | Houlihan, et al. | 549/283 |
| 3,880,886 | 4/1975 | Koch | 549/283 |
| 4,150,997 | 4/1979 | Hayes | 106/15.05 |
| 4,243,694 | 1/1981 | Mansukhani | 427/466 |
| 4,244,872 | 1/1981 | Gertisser, et al. | 549/288 |
| 4,328,332 | 5/1982 | Hayes et al. | 528/296 |
| 4,388,233 | 6/1983 | Bissell, et al. | 530/331 |
| 4,609,738 | 9/1986 | Möckli | 548/217 |
| 5,198,462 | 3/1993 | Natsugari, et al. | 514/432 |
| 5,248,784 | 9/1993 | Ohyama, et al. | 548/159 |
| 5,256,192 | 10/1993 | Liu et al. | 106/31.15 |
| 5,300,656 | 4/1994 | Kuckert et al. | 549/288 |
| 5,301,044 | 4/1994 | Wright | 358/500 |
| 5,424,320 | 6/1995 | Fortin, et al. | 514/337 |
| 5,565,292 | 10/1996 | Nakadera et al. | 430/109 |
| 5,574,078 | 11/1996 | Elwakil | 523/161 |
| 5,576,338 | 11/1996 | Friesen, et al. | 514/337 |
| 5,665,429 | 9/1997 | Elwakil | 427/218 |
| 5,674,314 | 10/1997 | Auslander et al. | 524/104 |
| 5,675,023 | 10/1997 | Igarashi, et al. | 549/400 |
| 5,679,724 | 10/1997 | Sacripante et al. | 523/161 |
| 5,681,381 | 10/1997 | Auslander et al. | 523/161 |
| 5,686,218 | 11/1997 | Liebermann et al. | 430/109 |
| 5,696,137 | 12/1997 | Heine, et al. | 514/322 |
| 5,696,157 | 12/1997 | Wang, et al. | 514/457 |
| 5,698,575 | 12/1997 | Watanabe, et al. | 514/383 |
| 5,776,932 | 7/1998 | Schindler, et al. | 514/235.2 |
| 5,834,130 | 11/1998 | Kido | 428/690 |
| 5,837,042 | 11/1998 | Lent et al. | 106/31.14 |
| 5,935,751 | 8/1999 | Matsuoka et al. | 430/110 |
| 5,936,008 | 8/1999 | Jones et al. | 523/161 |
| 6,001,936 | 12/1999 | Barrera, et al. | 525/454 |
| 6,007,955 | 12/1999 | Verhecken et al. | 430/106 |
| 6,017,671 | 1/2000 | Sacripante et al. | 430/110 |
| 6,034,121 | 3/2000 | O'Mahony, et al. | 514/456 |

OTHER PUBLICATIONS

Chemical Abstracts Service, Registry Handbook Number Section, 1998 Supplement, p. 8465R, Registry No. 213629–18–6, 1999.*

* cited by examiner

Primary Examiner—Fiona T. Powers
(74) Attorney, Agent, or Firm—Calfee, Halter & Griswold, LLP (57) ABSTRACT

Novel water soluble toners for use in ink jet printers, which are stable in water, and which have an acid number of greater than about 175, are provided. The toner, which is preferably fluorescent, is comprised of a novel, cycloaliphatic, polyester dye carrier; and a dye, preferably a fluorescent dye. The invention also relates to an ink which preferably comprises: an humectant, water and a toner dissolved in the water, and a base. The ink preferably has a viscosity less than about 10 cps, preferably less than about 6 cps, most preferably less than about 4 cps. The invention also relates to ink jet cartridges, and ink jet printers, which contain such novel ink, and also to a novel fluorescent yellow dye, which is useful in the novel fluorescent toner and ink jet printer inks. The invention also relates to methods of making such dye, the polyester dye carrier, and the ink jet cartridge.

4 Claims, 5 Drawing Sheets

INK JET PRINTING INKS

BACKGROUND OF THE INVENTION

Ink jet printer inks are typically prepared using water soluble dyes, or pigment dispersions, or toners, as the coloring agents. Fluorescent colorants are often unsuitable for ink jet printer inks. Fluorescent dyes alone are generally not suitable candidates for ink jet inks, because they require a polymeric dye carrier to provide bright, clean color.

Pigment dispersions contain a fluorescent dye associated with a polymeric carrier. However, the size of the pigment particles in the dispersion must be less than about 0.8 microns so the particles will not clog the print heads. Unfortunately, fluorescent pigments require extensive grinding to achieve such a particle size; such grinding is difficult, time consuming and expensive.

Fluorescent toners, which are fluorescent pigments which are soluble in water, eliminate the need for grinding. Such toners tend to be soluble in basic solutions and are typically acid functional; unfortunately, the toners are not stable to base hydrolysis and they hydrolyze over time. As the toner hydrolyzes, the pH of the solution drops which causes the toner to become insoluble and precipitate. The precipitated pigment clogs the print head and renders the ink unusable for ink jet printing. Thus, such inks have a short shelf life.

It would be desirable to have a fluorescent ink for use in ink jet printers which does not require grinding, is stable in water and does not clog printer heads.

SUMMARY OF THE INVENTION

The present invention provides a novel, water soluble toner, for use in inks particularly in ink jet printer ink, which is stable in water, does not clog printer heads, and which has an acid number of greater than about 175. The toner, which is preferably fluorescent, is comprised of a novel, alicycylic, polyester dye carrier; and at least one dye, preferably a fluorescent dye. The invention also relates to an ink concentrate which comprises the toner and a humectant, and also to the ink jet printer ink which preferably comprises: a humectant, water, a toner dissolved in the water, and a base. The ink jet printer ink preferably has a viscosity less than about 10 cps, preferably less than about 6 cps, most preferably less than about 4 cps. The invention also relates to ink jet cartridges, and ink jet printers, which contain such novel ink jet printer ink, and also to novel fluorescent Yellow BAC dyes, which are useful in the toners and ink jet printer inks. The invention also relates to methods of making such dyes, the polyester dye carrier and the toner.

DETAILED DESCRIPTION OF THE INVENTION

The present invention provides a novel toner for use in ink jet printers, which is soluble and stable in basic solutions. The toner, which is preferably fluorescent, is comprised of a novel, acid functional, alicyclic, polyester dye carrier and a dye, preferably a fluorescent dye. The invention also relates to inks which contain such novel toner and novel fluorescent Yellow BAC dyes, which are useful in the novel toner. The invention also relates to methods of making such Yellow BAC dyes, the polyester dye carrier and the fluorescent toner.

THE INK

The ink jet printer ink is preferably transparent and comprises: water and a toner dissolved in the water, such toner comprised of a polyester dye carrier and a dye, preferably a fluorescent dye; a humectant agent and a base, such as for example, strong bases such as for example group 1 hydroxides like sodium hydroxide, potassium hydroxide, cesium hydroxide, and weak bases such as for example, ammonium hydroxide, and alkanolamines such as triethanolamine. The base solubilizes the toner, more specifically the polyester dye carrier component of the toner, in water. Preferably the ink jet printer ink comprises: from about 0.1% to about 25%, more preferably from about 5 to about 20% of the toner; from about 0.1% to about 20%, more preferably from about 4% to about 15%, humectant; preferably from about 0.1 to about 20%, more preferably from about 3% to about 12%, base; and from about 15% to about 97%, more preferably from about 60% to about 75%, water.

The amount of toner present depends on the type of ink jet printer that the ink is used for. Many ink jet printers require that the ink have a viscosity of less than about 6 cps; some printers require inks with a viscosity of about 1 to 3 cps. The ink jet printer ink preferably has a viscosity less than about 10 cps, preferably less than about 6 cps, most preferably less than about 4 cps. An advantage of the inks of the present invention is that suitable viscosities can be achieved even with 25% toner in the ink. Generally it is preferred that there is from about 10% to about 25%, more preferably from about 13% to about 22% toner, most preferably about 20% toner in the ink.

The pH of the ink is preferably greater than 6.7, more preferably greater than 7. Preferably the ink has a pH of from about 6.7 to about 9, more preferably from about 7 to about 8. The ink preferably has an average rate of hydrolysis of less than about $9 \times 10^{-10}$ moles of ester/day.

Optionally, the ink also comprises a humectant, a surfactant to lower surface tension, and volatile alcohols to lower surface tension and lower viscosity. The humectant in ink jet printer ink prevents such ink from drying on the print head.

Suitable humectants are for example glycols, such as ethylene glycol, diethylene glycol, and dipropylene glycol. The humectant preferably has a viscosity less than about 100 cps, and preferably has about 100% miscibility in water.

The Ink Concentrate

The ink concentrate is primarily useful to prepare the ink such as the ink jet printer ink. The ink concentrate since it lacks the water volume present in the ink jet printer ink, is a more efficient than the ink jet printer ink for storage and shipping. The ink concentrate comprises the toner and a humectant.

In the ink concentrate, the humectant provides the ink with a viscosity which makes the ink readily dilutable with water to form an ink suitable for ink jet printing. Also the humectant prevents the toner in the ink concentrate from agglomerating.

In the ink concentrate, the humectant is added in an amount sufficient to render the toner liquid at 20° C., and to provide the toner with a viscosity of from about 5000 cps to about 250,000 cps, preferably from about 80,000 to about 150,000 cps at 20° C. Good results have been obtained using 100 grams propylene glycol per 100 grams of toner.

Suitable humectants are for example glycols, such as ethylene glycol, diethylene glycol, and dipropylene glycol. The humectant preferably has a viscosity less than about 100 cps, and preferably has about 100% miscibility in water.

THE TONER

The toner, which is preferably fluorescent, is comprised of a novel polyester dye carrier and a dye, preferably a fluorescent dye. The dye present from about 0.1% to about 20%, preferably from about 2% to about 10%, by weight, of the toner, and the polyester dye carrier is present from about 80% to 99.9%, preferably from about 90 to about 98%, by weight of the toner.

The Polyester Dye Carrier

The polyester dye carrier is a polyester polymer which has an acid number of at least about 175 mg KOH/1 g toner, preferably at least about 200 mg KOH/1 g toner. Preferably the polyester dye carrier has a melting point of from about 28° C. to about 55° C., more preferably from about 30° C. to about 45° C., most preferably from about 32° C. to about 41° C.

The polyester dye carrier preferably has a molecular weight of less than about 5,000. The polyester dye carrier preferably has a weight average molecular weight of from about 400 to about 5,000, more preferably from about 450 to about 2,000, most preferably from about 500 to about 1,000.

The polyester dye carrier is preferably comprised of polymerized units of a carboxylic acid monomer and a dihydric alcohol monomer. Either the carboxylic acid monomer or the dihydric alcohol monomer or both are alicyclic, and either the carboxylic acid monomer or the dihydric alcohol monomer or both, are acid functional. Thus, the polyester dye carrier contains alicyclic segments in the backbone of the polyester polymer, and the polyester dye carrier has acid groups attached to the backbone. Such acid groups are for example carboxylic acid groups. "Acid functional" as used herein with respect to the carboxylic acid monomer means the carboxylic acid monomer contains at least one acid group in addition to the two carboxylic acid groups. The term "carboxylic monomer" encompasses not only structures having carboxy groups but structures having the anhydrides thereof, as well.

The carboxylic acid monomer and dihydric alcohol monomer are present in the dye carrier, in a ratio of from about 1.35:1 to about 2:1, preferably from about 1.4:1 to about 1.7:1. The carboxylic acid monomer is an aliphatic carboxylic acid monomer or a cycloaliphatic carboxylic acid monomer and has at least two carboxylic acid groups. The carboxylic acid monomer preferably has the following structure:

HOOC—R—COOH

Wherein R is either an aliphatic chain having from 2 to 10 carbon atoms, or R is an alicyclic ring having from 5–8 carbon atoms. R is substituted or unsubstituted.

Suitable carboxylic acid monomers are, for example, cyclohexane dicarboxylic acid, particularly 1,4-cyclohexane dicarboxylic acid, and 1,2 cyclohexanedicarboxylic acid, adipic acid and succinic acid, and the anhydrides thereof.

The dihydric alcohol monomer is an aliphatic dihydric alcohol monomer or an alicyclic dihydric alcohol monomer. The dihydric alcohol monomer has at least two alcohol groups, and preferably has the following structure:

HO—R—OH

Wherein R is either an aliphatic chain having from 2 to 10, preferably from 3 to 6 carbon atoms, or R is an alicyclic ring having from 5 to 8 carbon atoms. R is substituted or unsubstituted.

Suitable dihydric alcohol monomers are for example, cyclohexanedimethanol, particularly 1,4-cyclohexanedimethanol, neopentyl glycol, 2-methyl-1,3-propanediol, ethylene glycol, propylene glycol, and dimethylol propionic acid.

Preferably, neither the dihydric alcohol monomer nor the carboxylic acid monomer contains an aromatic ring.

Preferably, though optionally, the polyester dye carrier is further comprised of polymerized units of monofunctional carboxylic acid monomers and or monofunctional alcohol monomers which act as chain terminators. Suitable monofunctional carboxylic acids are, for example, benzoic acid, isooctanic acid, isononanoic acid, neoheptanoic acid, neooctanoic acid, neononanoic acid, and neodecanoic acid. Suitable monofunctional alcohols are, for example, benzyl alcohol and cyclohexanol.

The Dye

Suitable fluorescent dyes are conventional fluorescent dyes which are preferably soluble in water, and preferably in alkaline aqueous solutions. Suitable dyes are for example, Basic Red 1, Basic Red 15, Basic Red 27, Basic Red 49, Acid Red 52, Acid Red 50, Basic Violet 10, Basic Violet 11, Basic Violet 15, Basic Violet 16, Basic Yellow 37 and Basic Yellow 40. Novel dyes such as for example Yellow BAC dyes are also useful. Preferably the dyes are pure and not salted so as to render them non-conductive.

Non-fluorescent water soluble dyes such as Acid Blue 9, Reactive Red 180, Reactive Red 120, and Acid Yellow 17, are also useful where a non-fluorescent ink is desired, or in combination with a fluorescent dye.

Typically, conventional fluorescent basic yellow dyes, coumarin yellow dyes and methine yellow dyes, are sensitive to alkaline degradation and will degrade before the blue or red dyes. However, the novel Yellow BAC dyes resist the alkaline degradation longer than conventional fluorescent yellow dyes. The Yellow BAC dyes have the following general structure:

wherein: $R_1$ and $R_2$ are H, $CH_2CH_3$, $CH_3$, but $R_1$ and $R_2$ are not both H;

$R_3$ is H, $SO_3H$, $SO_3Na$, Cl, Br, $SO_2NH_2$; and

$R_4$ is H or COOH.

The yellow BAC dye, 3-(benzimidazol-2-yl)-4-(2'-carboxyphenyl)-7-diethylaminocoumarine, has the following structure:

Preparation of the Yellow BAC Dye

The yellow BAC dyes are generally prepared by reacting a first reactant having the general structure:

wherein: $R_3$ is H, $SO_3H$, $SO_3Na$, Cl, Br, $SO_2NH_2$;

with a second reactant having the following general structure:

wherein: $R_1$ and $R_2$ are H, $CH_2CH_3$, $CH_3$, but $R_1$ and $R_2$ are not both H; and

$R_4$ is H or COOH.

The first reactant and the second reactant are preferably reacted in the presence of an acid, such as, for example, sulfuric acid, hydrochloric acid, acetic acid and pelargonic acid.

The particular Yellow BAC dye, 3-(benzimidazol-2-yl)-4-(2'-carboxyphenyl)-7-diethylaminocoumarine, is prepared by providing benzimidazole-2-acetonitrile and 2-(2'-carboxybenzoyl)-5-diethylaminophenol, then, reacting benzimidazole-2-acetonitrile and 2-(2'-carboxybenzoyl-5-diethylaminophenol, preferably in the presence of an acid such as for example sulfuric acid, hydrochloric acid, acetic acid and pelargonic acid. Benzimidazole-2-acetonitrile has the following structure:

The 2-(2'carboxybenzoyl)-5-diethylaminophenol has the following structure:

Example A

Benzimidazole-2-acetonitrile was prepared as follows. A mixture of o-phenylenediamine (1 mole) and ethyl cyanoacetate (2 moles) was refluxed for about 30 hours, cooled, diluted with propyl acetate (225 mL), filtered, washed and dried, to provide benzimidazole-2-acetonitrile in a 60–70% yield. Benzimidazole-2-acetonitrile is also available commercially from Aldrich Chemical Company.

2-(2'-Carboxybenzoyl)-5-diethylaminophenol was prepared as follows. A mixture of m-diethylaminophenol (1 mole) and phthalic anhydride (1.2 moles) was refluxed in toluene (2.0 L) for about 16 hours, cooled, and the resulting solid filtered, washed with toluene and dried to give 2-(2'-carboxybenzoyl)-5-diethylaminophenol in 70% yield.

Next, a mixture of benzimidazole-2-acetonitrile (1, 1 mole) and 2-(2'-carboxybenzoyl)-5-diethylaminophenol (2, 1 mole) was refluxed in dimethylformamide (800 mL) in the presence of concentrated sulfuric acid (4 moles) at about 150° C. for about 7 hours. The reaction mixture was cooled and filtered to remove insoluble impurities. To the filtrate was added 25% phosphorous acid (400 mL) at 100° C., cooled, filtered, washed with a 2:1 mixture of dimethylformamide and 25% phosphorous acid, 25% phosphorous acid followed by water, and the resulting product was dried to provide Yellow BAC Dye in about 50% yield.

Optical Brighteners

Optionally, the polyester dye carrier, the ink jet printer ink and the ink concentrate also contain an optical brightener, to improve the brightness of the color. Preferably the optical brightener is visible, for example glows a blue color, under black light, for example from about 250 to about 400 nm. Suitable optical brighteners are the Stilbenes, which are water soluble, for example Phorwite BA solution available from Bayer Chemical and Leucophor B 302 liquid available from Clariant.

Preparation of the Ink Concentrate, the Toner and the Ink

First the monomers are combined and reacted by heating the monomers. Good results have been obtained by heating to about 185° C. for two hours. Next, the dye is added and the material is cooled to provide a toner. Preferably the humectant is added while the toner is still warm to provide an ink concentrate which is a viscous liquid at room temperature and is readily soluble in alkali solutions. Good results have been obtained by cooling to about 153° C. and adding the humectant. The ink may be stored in the concentrated form; the humectant provides the ink with a viscosity which makes the ink concentrate readily dilutable to form an ink suitable for ink jet printing. Preferably when the ink jet printer ink is initially made it has a pH of from about 7.5 to about 8.

Figure 5:
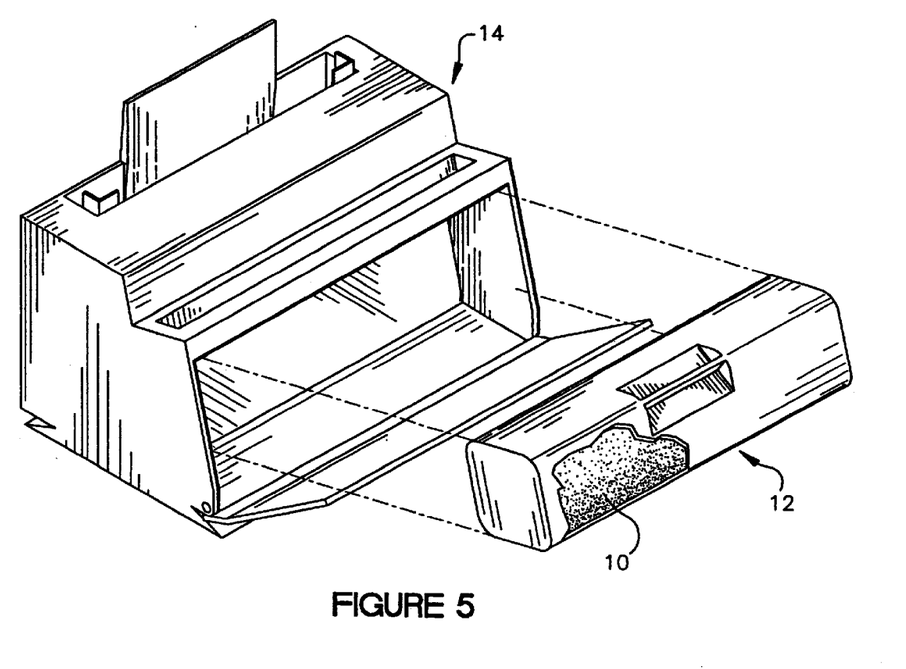
FIG. 5 is an exploded view of an ink jet printer, and an ink jet cartridge for insertion into the ink jet printer, said ink jet cartridge containing ink jet printing ink.

The ink jet printer ink is prepared by combining the ink concentrate with water, base and preferably surfactant. Good ink jet printer ink results have been obtained by combining the following: 20 g of the ink concentrate, 3 g 2-propanol, 9.5 g triethanolamine, 67.45 g water and 0.05 g Rhodapex Est-30 surfactant. With reference to FIG. 5, the ink jet printer ink 10 may be dispensed into conventional ink jet cartridges 12 which are used with conventional ink jet printers 14. As used herein, "cartridges" means not only the conventional unit of an ink reservoir and appended print head, but also encompasses other containers for ink jet printing ink which lack the print head, but are adapted to attach to ink jet printers. Such cartridges are well known in the art of ink jet printer fabrication.

It is also contemplated that cartridge systems comprises at least one cartridge containing a red ink; at least one cartridge containing a blue ink; and at least one cartridge containing a yellow ink; wherein at least one of the inks comprises the toner of the present invention.

Alternatively, rather than employing cartridges, particularly for large high volume jet printers such as used in commercial printing, the ink jet printing ink may be dispensed into high volume tanks, which are then connected to the print heads, via conventional equipment.

It is contemplated that the inks of the present invention fill not only in new cartridges, but also refill spent cartridges in ink jet printers. Techniques for refilling cartridges are known in the art.

EXAMPLES

Example 1

190 grams of dimethylolpropionic acid was combined with 280 grams of 1,4-cyclohexanedicarboxylic acid, 60 grams of benzoic acid and 37 grams of neopentyl glycol. The reaction was heated to 185° C. and held for two hours. After the two-hour hold, 18.5 grams of Basic Red 1 and 10.0 grams of Basic Violet 11 were added to the reaction. The reaction was then cooled to 135° C. upon which 345 grams of propylene glycol was added, to provide a concentrated, fluorescent ink. An ink jet printer ink was prepared by combining 20 g of the ink concentrate with 3 g 2-propanol, 9 g triethanolamine, 67.45 g water and 0.05 g Rhodapex Est-30 surfactant.

Example 2

89 grams of dimethylolpropionic acid was combined with 120 grams of 1,4-cyclohexanedicarboxylic acid. The reaction was heated to 185° C. and held for two hours. After the two-hour hold, 7.0 grams of Basic Red 1 and 5.0 grams of Basic Violet 11 was added to the reactor. The material was then cooled to 135° C. upon which 130 grams of propylene glycol was added, to provide a concentrated, fluorescent ink. An ink jet printer ink was prepared as in example 1 except that the ink of example 2 was used.

Example 3

95 grams of dimethylol propionic acid was combined with 132 grams of 1,2-cyclohexanedicarboxylic acid, 30 grams of benzoic acid and 18.5 grams of neopentyl glycol. The reaction was heated to 185° C. and held for two hours. After the two-hour hold, 9.5 grams of Basic Red 1 and 5.0 grams of Basic Violet 11 were added to the reaction and mixed at 170° C. for 15 minutes. The reaction was then cooled to 150° C. upon which 172 grams of diethylene glycol was added, to provide a concentrated, fluorescent ink. The ink was then cooled to 100° C., passed through a coarse paint filter and bottled. An ink jet printer ink was prepared as in example 1 except that the ink of example 3 was used.

Example 4

128 grams 2-methyl-1,3-propanediol was combined with 402 grams of 1,4-cyclohexanedicarboxylic acid, 60 grams of benzoic acid and 48 grams of dimethylol propionic acid. The reaction was heated to 185° C. and held for two hours. After the two-hour hold, 20.5 grams of Basic Red 1 and 11.0 grams of Basic Violet 11 were added to the reaction and mixed at 170° C. for 15 minutes. The reaction was then cooled to 150° C. upon which 190 grams of diethylene glycol was added, to provide a concentrated, fluorescent ink. The ink was then cooled to 100° C., passed through a course paint filter and bottled. An ink jet printer ink was prepared as in example 1 except that the ink of example 4 was used.

Example 5

190 grams of dimethylolpropionic acid was combined with 280 grams of 1,4-cyclohexanedicarboxylic acid, 60 grams of benzoic acid and 37 grams of neopentyl glycol. The reaction was heated to 185° C. and held for two hours. After the two-hour hold, 25 grams of yellow BAC dye was added. The reaction was heated to 190° C. and held for one hour. The reaction was then cooled to 150° C. upon which 345 grams of propylene glycol was added. The resulting material is a viscous liquid at room temperature and is readily soluble in alkali solutions.

Example 6

190 grams of dimethylolpropionic acid was combined with 280 grams of 1,4-cyclohexanedicarboxylic acid, 60 grams of benzoic acid and 37 grams of neopentyl glycol. The reaction was heated to 185° C. and held for two hours. The reaction was then cooled to 150 ° C., upon which 345 grams of propylene glycol was added. 50 grams of the optical brightener Phorwite BA Solution from Bayer Chemical was added. The resulting toner was a viscous liquid at room temperature and was readily soluble in alkali solutions.

Example 7

190 grams of dimethylolpropionic acid was combined with 280 grams of 1,4-cyclohexanedicarboxylic acid, 60 grams of benzoic acid and 37 grams of neopentyl glycol. The reaction was heated to 185° C. and held for two hours, then 35 grams of Acid Blue 9 was added. The reaction was then cooled to 150° C., upon which 170 grams of propylene glycol was added. The reaction was further cooled to 100° C., then 50 grams of the optical brightener Phorwite BA Solution from Bayer Chemical was then added. The resulting toner was a viscous liquid at room temperature and was readily soluble in alkali solutions.

COMPARATIVE EXAMPLES

Comparative Example 1

A fluorescent toner was prepared by reacting trimelitic anhydride, propylene glycol, and zinc acetate according to example 1 of U.S. Pat. No. 4,328,332. Although U.S. Pat. No. 4,328,332, does not disclose any dyes, a Rhodamine, specifically Basic Violet 11 and Basic Red 1, was used as in Example 1. Although an ink jet printer ink formulation is not disclosed in U.S. Pat. No. 4,328,332, the ink jet printer ink formulation of Example 1 was used; specifically, a comparative ink jet printer ink was prepared by combining 12.25 g of the toner with 8 g propylene glycol, 3 g 2-propanol, 9 g triethanolamine 67.45 g water and 0.05 Rhodapex Est-30 surfactant.

Comparative Example 2

A fluorescent toner was prepared by reacting trimelitic anhydride, neopentyl glycol, and zinc acetate according to example 2 of U.S. Pat. No. 4,328,332, using the dye as in Comparative Example 1. A comparative ink jet printer ink was prepared using the resulting toner, as in Comparative Example 1.

Comparative Example 3

A fluorescent toner was prepared by reacting trimelitic anhydride, neopentyl glycol, propylene glycol, and zinc acetate according to example 3 of U.S. Pat. No. 4,328,332 using the dye as in Comparative Example 1. A comparative ink jet printer ink was prepared using the resulting toner, as in Comparative Example 1.

Comparative Example 4

An ink jet printer ink was prepared as in Comparative Example 1, from an aromatic based, commercially available fluorescent toner.

EVALUATION

The ink jet printer inks of Examples 1, 3, 4 and 5 and the Comparative Examples were subjected to accelerated aging by placing in a convection oven at 50° C. Generally, Two to four weeks in the oven is considered to be about the equivalent to 1 year aging. The inks were periodically removed from the oven and evaluated.

Figure 1:
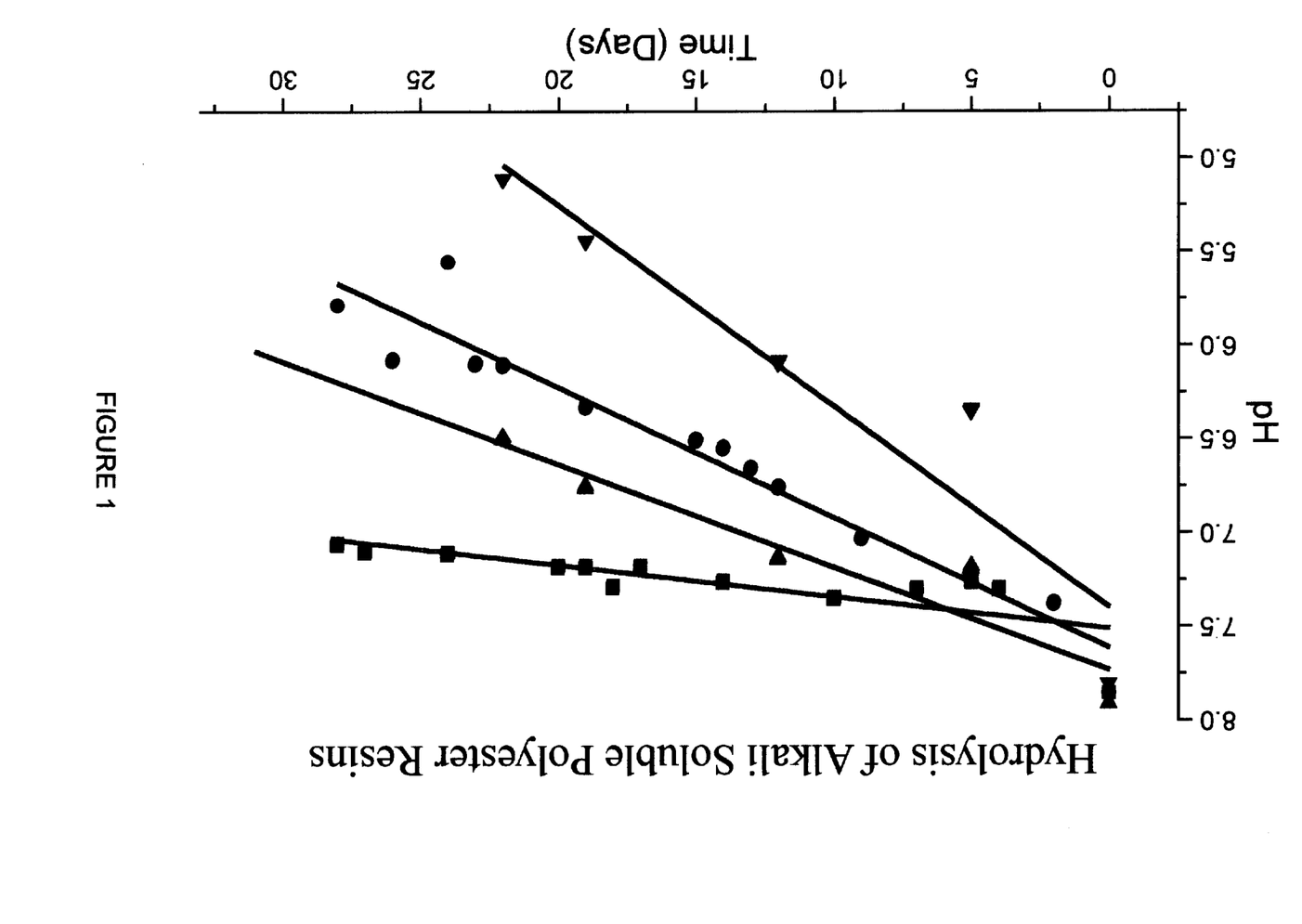
FIG. 1 is a graph showing the pH of the inks of Comparative Examples 1–3, and ink jet printer ink of Example 1, over time. The ink of Comparative Example 1 is indicated by a triangle, the ink of Comparative Example 2 is indicated by an inverted triangle and the ink of Comparative Example 3 is indicated by a circle. The plot of the ink jet printer ink of Example 1 is indicated by squares.
Figure 2:
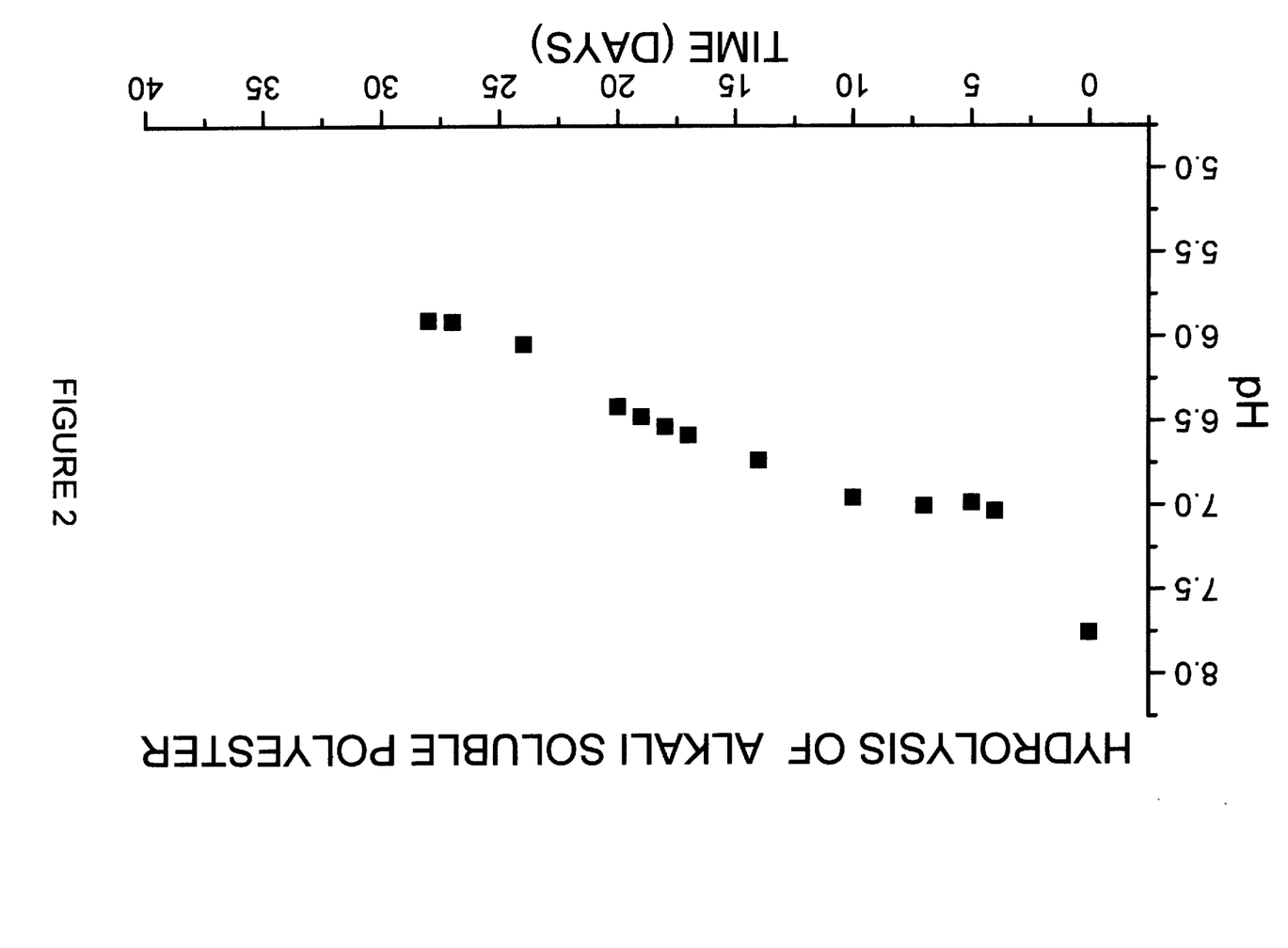
FIG. 2 is a graph showing the pH of the ink of Comparative Example 4, over time.

The pH was measured at each evaluation and the results plotted; the plots are shown in FIGS. 1 and 2. As shown in FIGS. 1 and 2, the pH of the inks of the Comparative Examples showed a significant drop in pH over time. This drop in pH indicates that the toner was hydrolyzed. (As the toner is hydrolyzed carboxylic acid groups are formed and are released which causes the pH to drop.) By day 3, the ink of Comparative Example 1 had a pH below 7; by day 17, the ink had a pH of about 5.1 and the toner had precipitated. By day 8, the ink of Comparative Example 2 had a pH below 7; by day 33 the ink had a pH of about 6.1 and the toner had precipitated. FIG. 1 shows the inks of Comparative Examples 1 and 2, designated by the squares and circles.

By day 4, the ink of Comparative Example 3 had a pH below 7; by day 28 the ink had a pH less than 6, and the toner had precipitated. By day 5 the ink of Comparative Example 4 had a pH less than 7; by day 25, the ink had a pH of less than 6 and the toner had precipitated. The pH of the inks of the Comparative Examples 3 and 4, designated by the triangles and circles, is shown in FIG. 2. Neither of the Comparative Examples contain polymerized units of an alicylic monomer.

In contrast, the ink jet printer ink of Example 1, remained in solution throughout the evaluation. The ink jet printer ink of Example 1 displayed only a minor initial drop in pH and after 35 days in the oven still had a pH of about 7.1.

Figure 3:
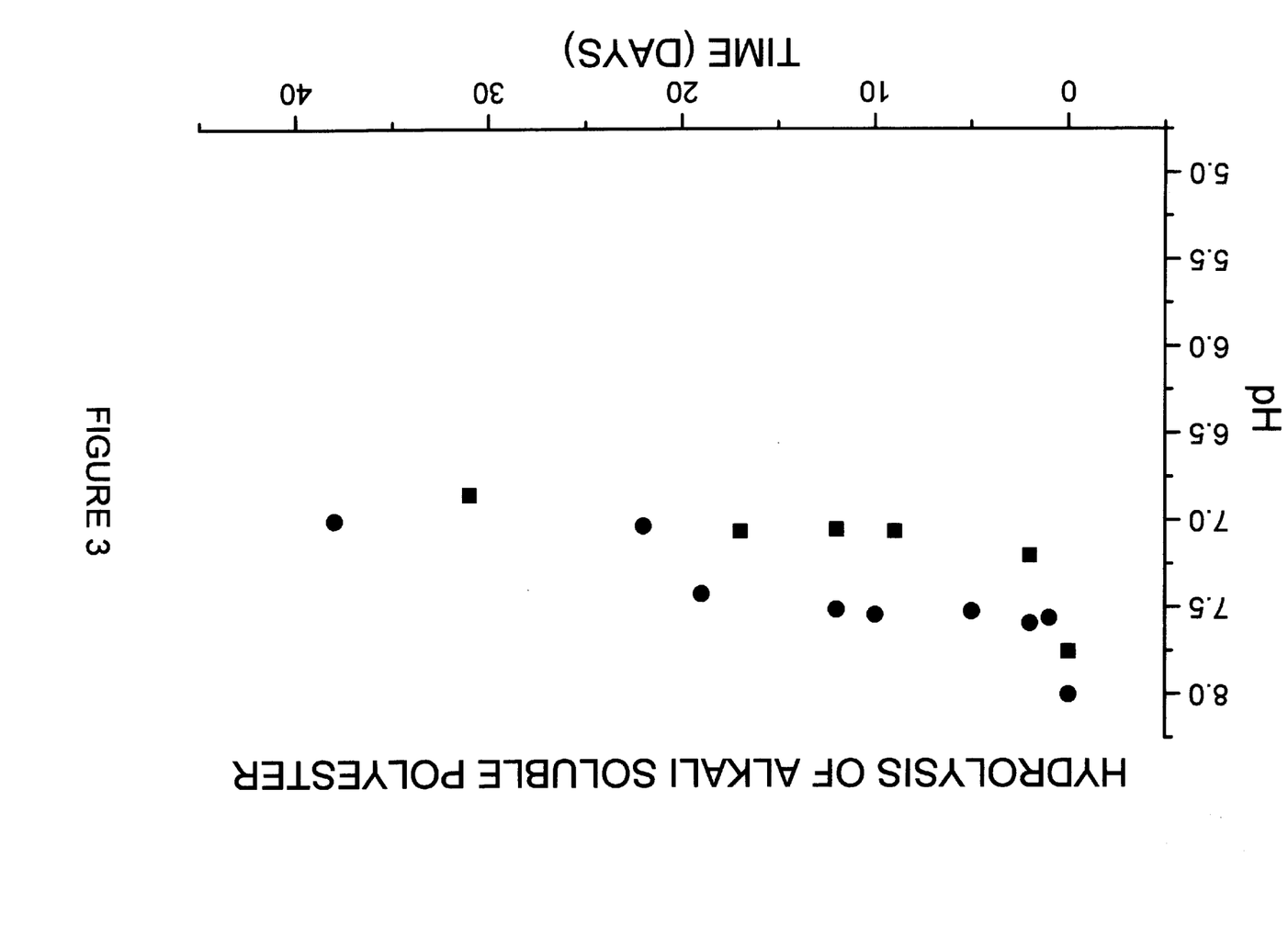
FIG. 3 is a graph showing the pH of two ink jet printer inks, of Examples 3 and 4 indicated by squares and circles. The graph shows the relatively consistent pH of the inks over time.
Figure 4:
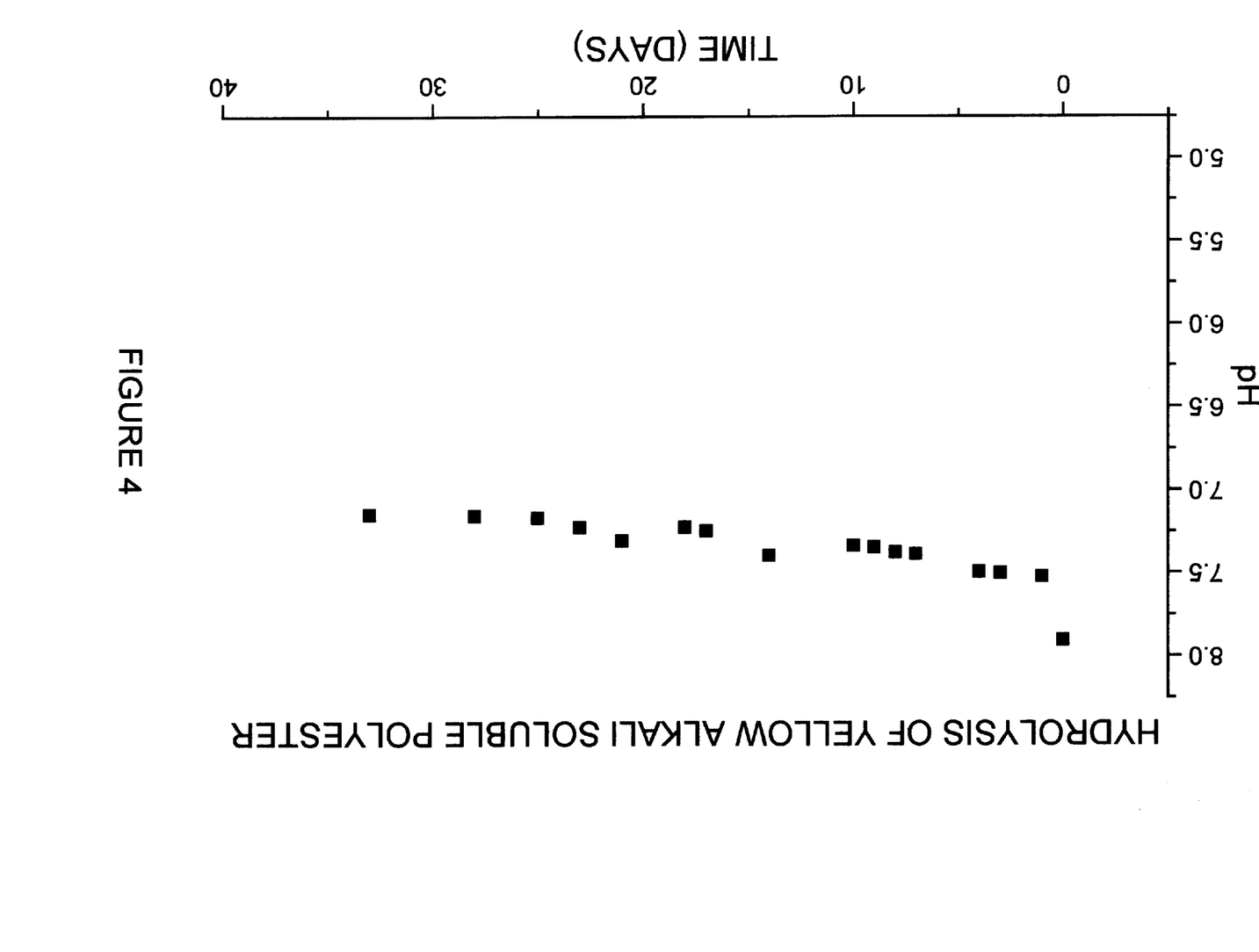
FIG. 4 is a graph showing the pH of the ink jet printer inks, of Example 5, which shows the relatively consistent pH of the ink over time.

Similarly, the ink jet printer inks of Examples 3 and 4 remained in solution, as shown in FIG. 3. Indeed by day 50 in the oven, the ink jet printer ink of Example 1 still had not precipitated.

An average rate of hydrolysis was determined for Comparative Examples 1–3 and the ink jet printer ink of Example 1. The rate of hydrolysis was determined by calculating difference in the moles of ester on day 1 and the day on which the toner precipitated in the ink. The ink jet printer ink of the examples did not precipitate. Accordingly for Example 1, day 35 was used as the second point for Example 1. The ink of Comparative Example 1 had a rate of hydrolysis of $4.58 \times 10^{-8}$ moles of ester/day. The ink of Comparative Example 2 had a rate of hydrolysis of $2.38 \times 10^{-9}$ moles of ester/day. The ink of Comparative Example 3 had a rate of hydrolysis of $5.88 \times 10^{-9}$ moles of ester/day.

In contrast, the ink jet printer ink of Example 1 had an average rate of hydrolysis of $2.33 \times 10^{-10}$ moles of ester/day.

Visual examination of the comparative inks revealed a progressive deterioration from day 1. For example, a visual examination of the ink of the Comparative Examples at day 31 revealed precipitation, weaker color, and a brownish tinge. In comparison, at 31 days in the oven, and indeed at 50 days, the ink jet printer ink of Example 1, did not have any precipitate, showed little change in color strength, hue, or viscosity. The ink jet printer ink of Example 1 was also deposited in a cartridge of a thermal ink jet printer and a continuous ink jet printer, where it performed satisfactorily.

While the inks such as for example ink jet printer inks and inks concentrates, toners, polyester dye carriers, and novel yellow dyes, have been described as being useful for ink jet printing, it is to be understood that the they are also useful as inks or colorants, or color concentrates for water based applications such as for water flexo-printing, pens, markers, and stamp pads. While the ink and toner have been described as being fluorescent, they also encompass non-fluorescent inks and toners as well.

What is claimed is:

1. A fluorescent yellow dye having the following structure:

wherein: $R_1$ and $R_2$ are H, $CH_2CH_3$, $CH_3$, but $R_1$ and $R_2$ are not both H;

$R_3$ is H, $SO_3H$, $SO_3Na$, Cl, Br, $SO_2NH_2$; and $R_4$ is H or COOH.

2. The dye of claim 1, wherein $R_1$ and $R_2$ are $CH_2CH_3$, $R_3$ is H, and $R_4$ is H.

3. A method for making a dye having the following structure:

wherein: $R_1$ and $R_2$ are H, $CH_2CH_3$, $CH_3$, but $R_1$ and $R_2$ are not both H;

$R_3$ is H, $SO_3H$, $SO_3Na$, Cl, Br, $SO_2NH_2$; and $R_4$ is H or COOH, comprising the following steps:
 a. providing a first reactant having the following structure:

wherein: $R_3$ is H, $SO_3H$, $SO_3Na$, Cl, Br, $SO_2NH_2$; and providing a second reactant having the following structure:

wherein: $R_1$ and $R_2$ are H, $CH_2CH_3$, $CH_3$, but $R_1$ and $R_2$ are not both H; and $R_4$ is H or COOH;

b. reacting the first reactant and the second reactant.

4. The method of claim 3, wherein $R_1$ and $R_2$ are $CH_2CH_3$, $R_3$ is H, and $R_4$ is H, the first reactant is benzimidazole-2-acetonitrile, and the second reactant is 2-(2'-carboxybenzoyl)-5-diethylaminophenol.

* * * * *